United States Patent
Lode et al.

(10) Patent No.: US 7,365,054 B2
(45) Date of Patent: Apr. 29, 2008

(54) METHODS FOR TREATMENT OF TUMORS AND METASTASES USING A COMBINATION OF ANTI-ANGIOGENIC AND IMMUNO THERAPIES

(75) Inventors: Holger N. Lode, Berlin (DE); Ralph A. Reisfeld, La Jolla, CA (US); David A. Cheresh, Encinitas, CA (US); Stephen D. Gillies, Carlisle, MA (US)

(73) Assignees: The Scripps Research Institute, La Jolla, CA (US); EMD Lexigen Research Center Corp., Billerica, MA (US)

( * ) Notice: Subject to any disclaimer, the term of this patent is extended or adjusted under 35 U.S.C. 154(b) by 0 days.

(21) Appl. No.: 11/527,029

(22) Filed: Sep. 26, 2006

(65) Prior Publication Data

US 2007/0036751 A1  Feb. 15, 2007

Related U.S. Application Data

(62) Division of application No. 09/502,732, filed on Feb. 11, 2000, now Pat. No. 7,115,261.

(60) Provisional application No. 60/119,721, filed on Feb. 12, 1999.

(51) Int. Cl.
*A61K 38/00* (2006.01)

(52) U.S. Cl. .............................. 514/9; 514/2; 424/85.1; 424/141.1; 424/130.1

(58) Field of Classification Search ..................... None
See application file for complete search history.

(56) References Cited

U.S. PATENT DOCUMENTS 5,753,230 A * 5/1998 Brooks et al. ........... 424/158.1
6,001,961 A * 12/1999 Jonczyk et al. ............. 530/317

OTHER PUBLICATIONS

Reisfeld.et.al. Antibody-interleukin 2 fusion protein: A new approach to cancer therapy. J.Clin.Lab.Anal.1996. vol. 10. 160-166.*
Lee.et.al. Efficacy of antitumor chemotherapy in C3H mice enhanced by the antiangiogenesis steroid, cortisone acetate. cancer. Res. 1987. vol. 47. 5021-5024.*
Xiang.et.al. Elimination of established murine colon carcinoma metastasis by antibody interleukin 2 fusion protein therapy. Cancer. Res.1997. vol. 57. 4948-4955.*
Folkman.J. Angiogenesis in cancer,vascular, rheumatoid and other diseases.Nat.med.1995. vol. 1; No. 1. 27-31.*

* cited by examiner

*Primary Examiner*—Misook Yu
(74) *Attorney, Agent, or Firm*—Olson & Cepuritis, Ltd.

(57) ABSTRACT

The invention provides methods for treating tumors and tumor metastases in a mammal comprising administering, to a mammal in need of treatment, a therapeutic amount of an antagonist sufficient to inhibit angiogenesis in combination with a therapeutic amount of anti-tumor immunotherapeutic agent, such as a anti-tumor antigen antibody/cytokine fusion protein having a cytokine and a recombinant immunoglobulin polypeptide chain sufficient to elicit a cytokine-specific biological response.

5 Claims, 4 Drawing Sheets

METHODS FOR TREATMENT OF TUMORS AND METASTASES USING A COMBINATION OF ANTI-ANGIOGENIC AND IMMUNO THERAPIES

CROSS-REFERENCE TO RELATED APPLICATIONS

This application is a division of U.S. application for patent Ser. No. 09/502,732 filed on Feb. 11, 2000, now U.S. Pat. No. 7,115,261, which claims priority to U.S. Provisional Application for Patent Ser. No. 60/119,721, filed Feb. 12, 1999, which are incorporated herein by reference.

STATEMENT OF GOVERNMENT RIGHTS

This invention was made with government support under Contract No. CA42508 by the National Institutes of Health. The government has certain rights in the invention.

TECHNICAL FIELD

The invention relates to methods for inhibition of primary tumors and metastases using a therapy based on the combined administration of an anti-angiogenic therapy and a targeted anti-tumor immunotherapy.

BACKGROUND

The generation of new blood vessels, or angiogenesis, plays a key role in the growth of malignant disease and has generated much interest in developing agents that inhibit angiogenesis (see for example Holmgren, L., O'Reilly, M. S. & Folkman, J. (1995) "Dormancy of micrometastases: balanced proliferation and apoptosis in the presence of angiogenesis suppression", *Nature Medicine* 1, 149-153; Folkman, J. (1995) "Angiogenesis in cancer, vascular, rheumatoid and other disease", *Nature Medicine* 1, 27-31; O'Reilly, M. S., et al., (1994) "Angiostatin: a novel angiogenesis inhibitor that mediates the suppression of metastases by a Lewis lung carcinoma", *Cell* 79, 315-328; Kerbel, R. S. (1997) "A cancer therapy resistant to resistance", *Nature* 390, 335-336; Boehm, T., et al., (1997) "Antiangiogenic therapy of experimental cancer does not induce acquired drug resistance", *Nature* 390, 404-7; and Volpert, O. V., et al., (1998) "A human fibrosarcoma inhibits systemic angiogenesis and the growth of experimental metastases via thrombospondin-1", *Proc. Natl. Acad. Sci. (U.S.A.)* 95, 6343-6348).

The use of $\alpha_v\beta_3$ integrin antagonists to inhibit angiogenesis is known in methods to inhibit solid tumor growth by reduction of the blood supply to the solid tumor. See, for example, U.S. Pat. No. 5,753,230 (Brooks & Cheresh) and U.S. Pat. No. 5,766,591 (Brooks & Cheresh) which describe the use of $\alpha_v\beta_3$ antagonists such as synthetic polypeptides, monoclonal antibodies and mimetics of $\alpha_v\beta_3$ that bind to the $\alpha_v\beta_3$ receptor and inhibit angiogenesis.

In addition, antibody-cytokine fusion protein therapies have been described which promote immune response-mediated inhibition of established tumors such as carcinoma metastases. For example, the cytokine interleukin 2 (IL-2) has been fused to a monoclonal antibody heavy chain immunoreactive with, in two separate fusion proteins, the tumor associated antigens epithelial cell adhesion molecule (Ep-CAM, KSA, KS1/4 antigen) or the disialoganglioside $GD_2$ by use of the antibodies KS1/4 and ch14.18, respectively, to form the fusion proteins ch14.18-IL-2 and KS1/4-IL-2, respectively. See, for example, U.S. Pat. No. 5,650,150 (Gillies).

The identification of vasculature-specific inhibitors of angiogenesis that are synergistic with therapies specifically targeting the tumor compartment, will allow for tailoring optimally effective cancer treatment.

Angiogenesis is characterized by invasion, migration and proliferation of endothelial cells, processes that depend on cell interactions with extracellular matrix components. In this context, the endothelial adhesion receptor of integrin $\alpha_v\beta_3$ was shown to be a key player by providing a vasculature-specific target for anti-angiogenic treatment strategies. (Brooks, P. C., Clark, R. A. & Cheresh, D. A. (1994) "Requirement of vascular integrin alpha v beta 3 for angiogenesis", *Science* 264, 569-571; Friedlander, M., et al., (1995) "Definition of two angiogenic pathways by distinct alpha v integrins", *Science* 270, 1500-1502). The requirement for vascular integrin $\alpha_v\beta_3$ in angiogenesis was demonstrated by several in vivo models where the generation of new blood vessels by transplanted human tumors was entirely inhibited either by systemic administration of peptide antagonists of integrin $\alpha_v\beta_3$ or anti-$\alpha_v\beta_3$ antibody LM609. (Brooks, P. C., et al., (1994) *Science* supra; Brooks, P. C., et al., (1994) "Integrin alpha v beta 3 antagonists promote tumor regression by inducing apoptosis of angiogenic blood vessels", *Cell* 79, 1157-1164). Murine hybridoma LM609 has been deposited with the American Type Culture Collection (ATCC, Manassas, Va., USA) as the International Depository Authority under the Budapest Treaty, and assigned the ATCC Designation HB 9537, on Sep. 15, 1987. Such antagonists block the ligation of integrin $\alpha_v\beta_3$ which promotes apoptosis of the proliferative angiogenic vascular cells and thereby disrupt the maturation of newly forming blood vessels, an event essential for the proliferation of tumors.

Vascular Endothelial Growth Factor (VEGF) has been identified as a selective angiogenic growth factor that can stimulate endothelial cell mitogenesis. Human tumor biopsies exhibit enhanced expression of VEGF mRNAs by malignant cells and VEGF receptor mRNAs in adjacent endothelial cells. VEGF expression appears to be greatest in regions of tumors adjacent to avascular areas of necrosis. (for review see Thomas et al., (1996) "Vascular Endothelial Growth Factor, a Potent and Selective Angiogenic Agent", *J. Biol. Chem.* 271(2): 603-606). Effective anti-tumor therapies may utilize targeting VEGF receptor for inhibition of angiogenesis using monoclonal antibodies. (Witte L. et al., (1998) "Monoclonal antibodies targeting the VEGF receptor-2 (Flk1/KDR) as an anti-angiogenic therapeutic strategy", *Cancer Metastasis Rev.* 17(2):155-61.

A major obstacle for effective treatment of disseminated malignancies includes minimal residual disease characterized by micrometastases that lack a well-established vascular supply for delivery of therapeutics. In this regard, a novel immunotherapeutic strategy proved efficient in using tumor compartment-specific monoclonal antibodies to direct cytokines to the tumor microenvironment. This was achieved by recombinant antibody-cytokine fusion proteins, generated to maintain the unique tumor-specific targeting ability of monoclonal antibodies and the immunomodulatory functions of cytokines. The use of an antibody-IL-2 fusion protein to direct IL-2 into the tumor compartment induced activation of effector cells invading the tumor microenvironment and resulted in efficient eradication of established micrometastases in three different syngeneic mouse tumor models. (Becker, J. C., et al. (1996) "T cell-mediated eradication of murine metastatic melanoma induced by targeted interleukin 2 therapy", *J_Exp. Med* 183, 2361-2366; Xiang, R., et al., (1997) "Elimination of established murine colon carcinoma metastases by antibody-interleukin 2 fusion protein therapy", *Cancer Res.* 57, 4948-4955; Lode, H. N., et al., (1998) "Natural killer cell-mediated eradication of neuroblastoma metastases to bone marrow by targeted interleukin-2 therapy", *Blood* 91, 1706-1715). Although quite effective at early stages of tumor metastasis, this tumor compartment-directed approach could only delay growth of metastases at later stages of tumor growth characterized by a fully developed vascular compartment. Here, we addressed the question of whether there is a complementary advantage of specific vascular and tumor compartment-directed treatment strategies being synergistic when used in sequential and simultaneous combinations.

This was tested in three syngeneic murine tumor models of colon carcinoma, melanoma and neuroblastoma, the latter characterized by spontaneous hepatic metastases. All three models exhibit close similarities to the diseases in humans. The melanoma and neuroblastoma models express disialoganglioside GD2, a well-established tumor-associated antigen in such neuroectodermal malignancies (Irie, R. F., Matsuki, T. & Morton, D. L. (1989) "Human monoclonal antibody to ganglioside GM2 for melanoma treatment", *Lancet* 1, 786-787; Handgretinger, R., et al., (1995) "A phase I study of human/mouse chimeric antiganglioside GD2 antibody ch14.18 in patients with neuroblastoma", *Eur. J. Cancer* 31A, 261-267) and the colon carcinoma model is characterized by the expression of the epithelial cell adhesion molecule (Ep-CAM, KSA, KS1/4 antigen), a target molecule successfully exploited for passive immunotherapy in man (Riethmuller G., et al., (1994) "Randomised trial of monoclonal antibody for adjuvant therapy of resected Duke's C colorectal carcinoma", *Lancet* 343, 1177-1183). These antigens specifically delineate the tumor compartment in these models targeted by the antibody-interleukin-2 fusion proteins with human/mouse chimeric anti-GD2 antibody (ch14.18-IL-2)(Gillies, S. D., et al., (1992) "Antibody-targeted interleukin 2 stimulates T-cell killing of autologous tumor cells", *Proc. Natl. Acad. Sci. (U.S.A.)* 892, 1428-1432) and humanized anti-Ep-CAM (anti-KSA, anti-KS1/4 antigen) antibody KS1/4-IL-2 (Xiang, R., et al. (1997) supra.; Gillies, S., et al, (1998) "Antibody-IL-12 fusion proteins are effective in SCID mouse models of prostrate and colon carcinoma metastases", *J Immunol.* 160, 6195-6203). The vascular compartment of these tumor models, as described in several animal models, is defined by expression of integrin $\alpha_v\beta_3$ on newly formed blood vessels. (Brooks, P. C., et al., (1994) supra). The data presented here demonstrate a synergistic efficacy of simultaneous and sequential treatments specifically targeting tumor and vascular compartments of primary tumors and distant metastases. A mechanism for this synergism is provided by a decrease in blood vessel formation and an increase in inflammation only in animals treated with the combination therapy. These observations emphasize the beneficial effect of combining anti-angiogenic with tumor-specific anti-tumor immunotherapeutic approaches.

SUMMARY OF THE INVENTION

The present invention is directed to a method for treating a tumor cell in a patient in need of such treatment, comprising administering to said patient a tumor cell proliferation inhibiting amount of an angiogenesis inhibiting agent and an anti-tumor immunotherapy agent. Inhibition of tumor cell proliferation can encompass inhibition of the growth of tumor cells in existing tumor or tumor metastases, inhibition of the formation of additional tumor metastases, and even tumor cell death. The angiogenesis inhibiting agent and the anti-tumor immunotherapy agent can be administered substantially concurrently as well as sequentially.

In one embodiment, the present invention describes a method for treating a tumor or tumor metastases in a patient by the administration to a patient of the combination of at least one angiogenesis inhibiting agent and at least one anti-tumor immunotherapeutic agent. An effective inhibition of tumor cell proliferation in said patient can be achieved in this manner.

The patient can receive the aforementioned therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

An angiogenesis inhibiting agent suitable for use in the methods of the invention is one which can inhibit the formation of new blood vessels (neovascularization) or enlargement of existing capillary networks into the tissues near a tumor cell. Suitable angiogenesis inhibiting agents can be peptides with angiogenesis inhibiting activity, such as the tumor associated antigen PSA. Other suitable angiogenesis inhibiting agents can be antagonists of VEGF associated angiogenesis, for example antagonists of the VEGF receptor on the surface of cells. A preferred angiogenesis inhibiting agent is an antagonist of $\alpha_v\beta_3$ integrin binding to cells. An $\alpha_v\beta_3$ antagonist for use in the methods of the invention is one that can inhibit angiogenesis in a tumor or tumor metastases associated tissue, when administered to the targeted tissue or cells. Such antagonists can be unique linear or cyclo-polypeptides, linear or cyclo-RGD-containing polypeptides, antibodies, or mimetics of $\alpha_v\beta_3$ that bind to the $\alpha_v\beta_3$ receptor and inhibit angiogenesis.

Where the $\alpha_v\beta_3$ antagonist is an antibody, it is contemplated that such can be polyclonal, monoclonal, or an antigen binding fragment thereof, having antigen binding specificity for $\alpha_v\beta_3$ or the $\alpha_v\beta_3$ receptor. A preferred monoclonal antibody which binds to $\alpha_v\beta_3$ integrin is the monoclonal antibody identified as LM609 (ATCC HB 9537).

A preferred angiogenesis inhibiting agent is a polypeptide which is an $\alpha_v\beta_3$ receptor antagonist that can inhibit the integrin receptor on target cells. A most preferred embodiment of an $\alpha_v\beta_3$ antagonist is the synthetic RGD-containing peptide cyclo(RGDfN-MeV) (SEQ ID NO: 11) and the like. Cyclic peptides of this general type are described in U.S. Pat. No. 5,262,520 (Plow et al.). Non-RGD containing peptides are described in U.S. Pat. No. 5,780,426 (Palladino et al.).

An anti-tumor immunotherapy agent suitable for use in the methods of the invention is an immunotherapeutic agent which comprises a cell effector component joined to a tumor associated antigen targeting component. Suitable cell effector components can include cytotoxic chemicals, cytotoxic radioisotopes, and cell signaling agents such as cytokines.

Suitable tumor targeting components are polypeptide chains which bind to tumor associated antigens present on or in the surrounding tissue matrix of a tumor cell such as receptor protein chains or immunoglobulin chains.

Tumor associated antigens which can be used for targets of the immunotherapeutic agents include a tumor associated antigen selected from the group consisting of AFP, CA 125, CEA, CD19, CD20, CD44, CD45, EGF Receptor, $GD_2$, $GD_3$, GM1, GM2, Her-2/Neu, Ep-CAM (KSA), IL-2 receptor, Lewis-Y, Lewis-X (CD 15), melanoma-associated proteoglycan MCSP, PSA and Transferrin Receptor.

The preferred immunotherapeutic agent has an effector component that is a cytokine polypeptide joined to a targeting component which is an immunoglobulin (Ig) polypeptide chain. The Ig polypeptide chain comprises a variable region which binds to a tumor associated antigen. It is preferred that said immunoglobulin chain, when combined with the appropriate complementary chain (i.e. a heavy chain complements a light chain) defines an antibody active site which is specific for a tumor associated antigen.

The tumor targeting Ig portion of the immunotherapeutic agent may comprise an entire immunoglobulin chain amino acid sequence, or at least the fragment of which comprises the antigen binding specificity portion of the protein. Thus, a suitable Ig polypeptide chain will have at least an Ig variable region specific for a tumor associated antigen.

An antibody and polypeptide chains therefrom, suitable for use in the methods of the invention, will have an amino acid sequence that can be of any mammalian origin. Where such antibody protein is not of the same origin as the anticipated patient, fragments of the antibody protein, such as F(ab')2, Fab, Fv or engineered Fv single chain antibody protein can be used. To further reduce antigenicity of the antibody protein, modification of the antibody amino acid sequence may be accomplished to reduce such by making the protein appear more like the patients normal antibody components. For example, monoclonal murine antibody amino acid sequences can be modified to appear more human, for administration to human patients by a variety of processes for humanization of the antibody.

Alternatively, the antibody can be of human origin (genetically encoded for by human Ig genes) but produced in a transgenic animal transformed to express the human Ig genes instead of their own native Ig genes. For example transgenic mice can be constructed which express human origin DNA encoding for human Ig proteins. Generation of monoclonal antibody from such transgenic mice will result in murine B-cell hybridomas expressing human DNA encoding for antibodies having human origin amino acid sequences. This will greatly reduce the immunogenicity of such antibodies for use in treating human patients.

For treating human patients, preferred antibodies for use in the method of the claimed invention are the humanized anti-GD2 tumor associated antigen monoclonal antibody ch14.18 and the anti-KS1/4 tumor associated antigen (also known as Ep-CAM and KSA) monoclonal antibody KS1/4.

A cell-effector component of an immunotherapeutic suitable for use in the methods, compositions and kits embodying the present invention is a cytokine selected from the group consisting of BDNF, CNTF, EGF, Epo, FGF, Flt3L, G-CSF, GM-CSF, I-309/TCA-3, gamma-IP-10, IFN alpha, IFN beta, IFN gamma, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, LIF, LT, MCP-1 through MCP-3, M-CSF, MIF, MIP-1alpha, MIP-1beta, MIP-2, NGF, NT-3, NT-4, OSM, PBP, PBSF, PGFD, PF-4, RANTES, SCF, TGF alpha, TGF beta, TNF alpha, Tpo and VEGF. Suitable cytokine that is a chemokine, can be selected from the group consisting of C10, EMF-1, ENA-78, Eotaxin, GCP-2, HCC-1, I-309, IL-8, IP-10, Lymphotactin, MCP-1, MCP-2, MCP-3, MGSA, MIG, MIP-1alpha, MIP-1beta, MIP-2, NAP-2, PF4, RANTES, SCM-1 and SDF-1. The cytokine portion of the aforementioned immunotherapeutic agent can be the entire cytokine protein amino acid sequence, or a fragment of such fusion protein sufficient to elicit a cytokine-specific biological response.

In a preferred embodiment, the cytokine portion of the immunotherapeutic has biological activity of IL-2.

In an immunotherapeutic agent comprising a cytokine polypeptide joined to an Ig polypeptide, a suitable junction between a cytokine polypeptide chain and an Ig polypeptide chain includes a direct polypeptide bond, a junction having a polypeptide linker between the two chains, or other chemical linkage between the chains including the use of biotinylation and the avidin-biotin complex. A preferred junction is either a direct or polypeptide linker spaced polypeptide linkage. This direct linkage allows for the expression of the immunotherapeutic agent as a single fusion protein, from a host cell transformed with a suitable expression vector encoding for the fusion protein immunotherapeutic agent.

Thus a preferred immunotherapeutic agent for use in the methods of the invention is a bifunctional fusion protein having a cytokine component and a tumor associated antigen targeting component where the targeting component is an Ig polypeptide chain which has specificity for a tumor associated antigen. Examples of such preferred immunotherapeutic agents include the GD2 targeted fusion protein ch14.18-IL2, and the KS1/4 tumor associated antigen (also known as Ep-CAM and KSA) targeted fusion protein KS1/4-IL2.

Alternatively, another immunotherapeutic suitable for use in the methods, compositions and kits of the invention can have a cell effector component that is a cytotoxic agent. A suitable cytotoxic agent is one which has a direct cytotoxic effect on the tumor cell, ie. immunotoxins, radioisotopes, cytotoxic drugs, and the like. Like cytokine immunotherapeutics described above, cytotoxic peptides can be joined to the tumor associated antigen targeting Ig polypeptide to form a fusion protein either directly, or spaced by a linker peptide or chain. Chemical linkage of chemical cytotoxins to the targeting Ig chains can be made. Radioisotope bearing antibody chains can also be constructed.

Another aspect of the invention encompasses a therapeutic composition comprising an angiogenesis inhibiting agent and an anti-tumor immunotherapeutic agent. It is preferred that the anti-tumor immunotherapeutic agent targets tumor or tumor metastases cells by having a tumor associated antigen specificity component joined to a cell effector component. In a preferred therapeutic composition of the invention the anti-tumor immunotherapeutic agent is a bifunctional protein having an effector component that is a cytokine polypeptide joined to a tumor targeting component that is an immunoglobulin (Ig) polypeptide chain, where said Ig chain comprises a variable region which binds to a tumor associated antigen.

Yet another aspect of the invention is a kit for treating a tumor or tumor metastases. The kit comprises a package containing an angiogenesis inhibiting agent, such as an $\alpha_v\beta_3$ antagonist capable of inhibiting angiogenesis in said tumor or said tumor metastases; a bifunctional protein component having a cytokine activity and tumor antigen specificity; and instructions for treating tumor cells in tumors and tumor metastases. The kit can also include specific labeling indicating the use of the kit components for treating a tumor or tumor metastases.

BRIEF DESCRIPTION OF THE DRAWINGS

Preferred embodiments of the invention are described below with reference to the following accompanying drawings wherein:

FIG. 1 graphically depicts the effect of a combined therapy with anti-angiogenic $\alpha_v$ integrin antagonist and anti-tumor compartment-specific immunotherapy with antibody-IL-2 fusion proteins on primary tumors.

FIG. 2 graphically depicts the effect of combined antivascular and anti-tumor therapies on vascularization and anti-tumor immune response.

DETAILED DESCRIPTION OF THE INVENTION

Figures 1A, 1B, 1C:
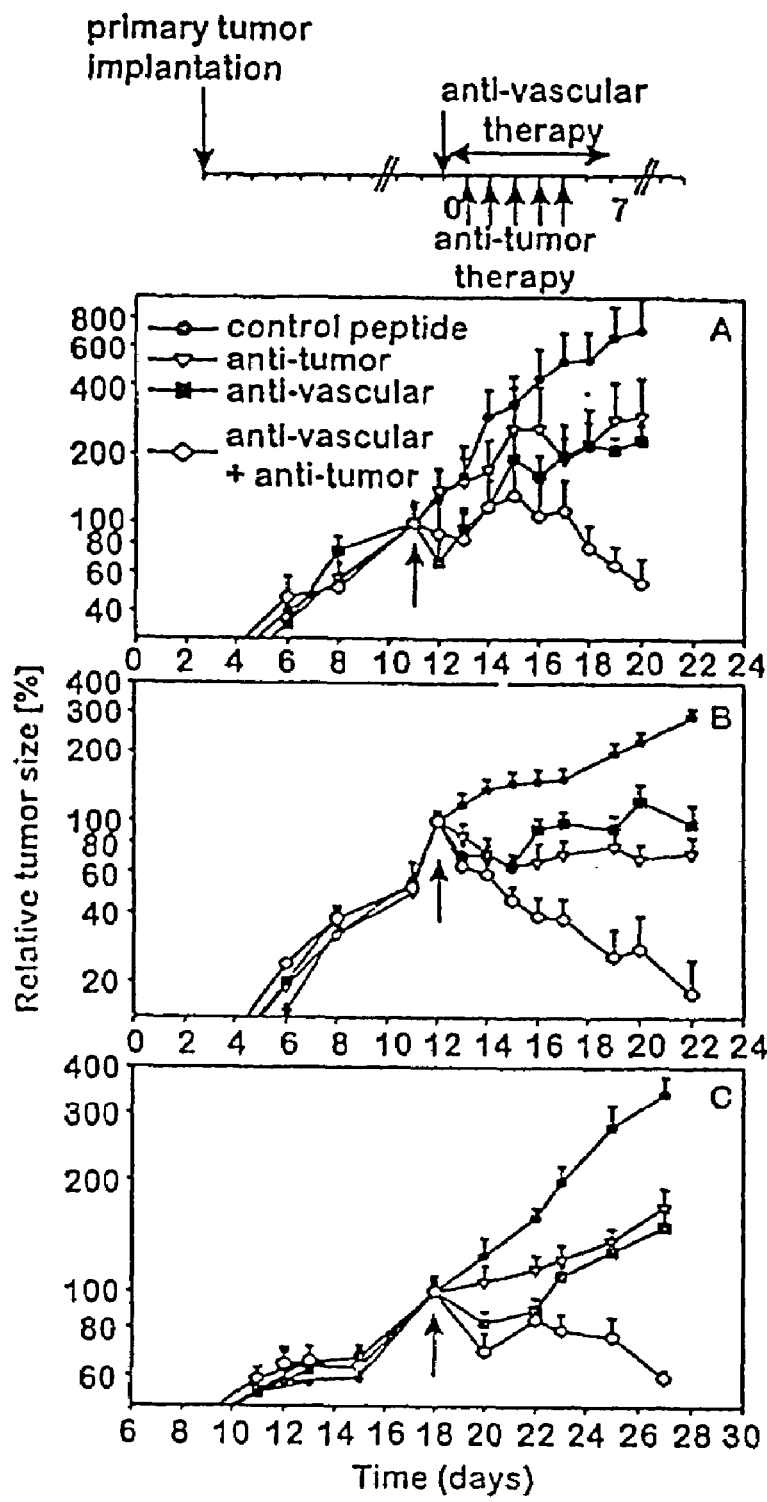
FIG. 1A depicts results from primary tumors induced by subcutaneous injection ($2 \times 10^6$) of NXS2 neuroblastoma.
FIG. 1B depicts results from primary tumors induced by subcutaneous injection ($2 \times 10^6$) of CT26-KSA colon carcinoma.
FIG. 1C depicts results from primary tumors induced by subcutaneous injection ($2 \times 10^6$) of B78-D 14 melanoma cells.

The suppression and eradication of primary tumors and distant metastases is a major goal of alternative treatment strategies for cancer, such as inhibition of angiogenesis and targeted immunotherapy.

It has now been discovered that there is an unexpected synergy in effectiveness at treating tumor cells in tumors and tumor metastases by the combined use of the two therapeutic modalities referred to herein as (1) (anti-angiogenic) angiogenesis inhibition therapy and (2) anti-tumor immunotherapy. In particular, combined $\alpha_v$ antagonist therapy and anti-tumor antigen/cytokine fusion protein therapy is described.

It was found that a synergy occurs between two unique monotherapies directed against vascular and tumor compartments; respectively, a tumor vasculature-specific anti-angiogenic integrin $\alpha_v$ antagonist and tumor-specific antibody-interleukin-2 fusion proteins.

Simultaneous and sequential combination of these monotherapies effectively eradicated spontaneous liver metastases in a poorly immunogenic syngeneic model of neuroblastoma. This was in contrast to controls subjected to monotherapies with either an anti-angiogenic integrin $\alpha_v$ antagonist or antibody-IL-2 fusion proteins, which were only partially effective at the dose levels applied.

Furthermore, simultaneous treatments with the integrin $\alpha_v$ antagonist and tumor-specific antibody-IL-2 fusion proteins induced dramatic primary tumor regressions in three syngeneic murine tumor models, i.e. melanoma, colon carcinoma and neuroblastoma. However, each agent used as monotherapy alone, induced only a delay in tumor growth.

The anti-tumor response was accompanied by a simultaneous 50% reduction in tumor vessel density and a five-fold increase in inflammatory cells in the tumor microenvironment. Subsequently, tumor necrosis was demonstrated only in animals receiving the combination therapy, but not when each agent was applied as monotherapy. The results show that these synergistic treatment modalities provide a novel and effective tool for future therapies of metastatic cancer.

The invention describes methods for treatment of tumors and tumor metastases, therapeutic compositions and therapeutic kits (packaged systems) useful for practicing the synergistic therapies described herein.

1. Therapeutic Compositions

A variety of therapeutic compositions are described which are useful in practicing the methods of the invention. The compositions include (anti-angiogenesis) angiogenesis inhibiting reagents such as $\alpha_v\beta_3$ antagonists and anti-tumor agents such as tumor antigen/cytokine fusion proteins, either alone or in various combinations.

A. Angiogenesis Inhibitor

Angiogenesis inhibitors which inhibit angiogenesis in tissues treated therewith can be used in the compositions and methods of the invention. A preferred angiogenesis inhibitor is an αv antagonist, and in particular a $\alpha_v\beta_3$ antagonist. An angiogenesis inhibiting (anti-angiogenesis) $\alpha_v\beta_3$ antagonist can be a peptide, a RGD-containing peptide, an anti-$\alpha_v\beta_3$ antibody, an anti-$\alpha_v\beta_3$ receptor antibody, or an $\alpha_v\beta_3$ mimetic. Exemplary $\alpha_v\beta_3$ antagonists are described in the teachings of U.S. Pat. No. 5,753,230 (Brooks & Cheresh) and U.S. Pat. No. 5,766,591 (Brooks & Cheresh), the disclosures of which relating to the preparation and use of an $\alpha_v\beta_3$ antagonist are specifically incorporated herein by reference.

Preferred antagonists are RGD-containing peptides, such as the cyclic peptide cyclo(RGDfN-MeV) (SEQ ID NO: 11). Additional antagonists have been described in the literature including organic mimetics, and non-RGD containing cyclic-peptides which function as $\alpha_v\beta_3$ antagonists. See, for example Brooks et al., International Publication No. WO 97/45137, (PCT/US97/09158).

Assays for the identification of an $\alpha_v\beta_3$ antagonist suitable for use as an antagonist are described in the referenced U.S. patents, and therefore it is considered that alternate antagonists can be readily identified for practicing the present invention.

Suitable anti-$\alpha_v\beta_3$ monoclonal antibody can be modified to encompasses antigen binding fragments thereof, including F(ab)2, Fab, and engineered Fv or single-chain antibody (SCA). Methods for preparing such fragments are known in the art (see for example Hermanson, G. T., *Bioconjugate Techniques*, Academic Press, 1996). The methods of the invention describing antibody use also incorporates the suitable modification of whole antibody to antigen binding fragments thereof. One suitable monoclonal antibody is identified as LM609 (ATCC HB 9537).

Other $\alpha_v\beta_3$ receptor antagonists have been shown to be effective in inhibiting angiogenesis, and would be suitable for use in the methods of the invention. For example, chemical receptor antagonists such as (S)-10,11-Dihydro-3-[3-(pyridin-2-ylamino)-1-propyloxy]-5H-dibenzo[a,d]cycloheptene-10-acetic acid (known as SB-265123) have been tested in a variety of mammalian model systems. (see for example, Keenan R M et al., (1998) *Bioorg. Med. Chem. Lett.* 8(22): 3171-6; Ward K W et al., (1999) *Drug Metab. Dispos.* 27(11): 1232-41).

Vascular Endothelial Growth Factor (VEGF) has been identified as a selective angiogenic growth factor. Thus, an alternative or additional angiogenesis inhibiting agent can be an inhibitor of VEGF activity sufficient to inhibit angiogenic growth. Such an inhibitor could be a competitive inhibitor or a VEGF binding/inactivating molecule, or a VEGF receptor antagonist. For example, possible inhibitors could be a non-angiogenic chemical mimic of VEGF to compete for binding to the VEGF target/receptor, a modified non-angiogenic VEGF derivative, an antibody which specifically binds VEGF sufficient to inhibit the angiogenic activity, or possibly another specific protein which binds VEGF (such as isolated VEGF receptor protein), or antibody which binds to VEGF receptor and blocks interaction with VEGF.

Other compounds have been identified on the basis of the ability for the compound to inhibit angiogenesis, for example isolated tumor associated antigen PSA.

B. Anti-Tumor Immunotherapeutic

The methods and compositions for use in such methods of the invention contemplate the combined administration of at least one (anti-angiogenesis) angiogenesis inhibiting therapeutic with at least one, anti-tumor immunotherapeutic agent. The preferred anti-tumor immunotherapeutic agent combines a tumor targeting component with a cell effector component, such as a cytokine, immunotoxin, radioactive agent or the like. The tumor targeting component preferably comprises at least the antigen binding portion of an antibody directed towards a tumor associated antigen. In one preferred embodiment, the effector component is a cytokine.

a) Tumor Associated Antigens

Tumor associated antigen are the target by which the immunotherapeutic agent for use in the methods, compositions and kit of the invention, is ultimately targeted to the tumor cell. Tumor associated antigens are recognized in the art to be correlated with certain types of cancer. In most all cases the tumor associated antigens are cell surface antigens which are expressed in a manner not normally found for the normal cells associated with the origin of the cancer tumor. Other tumor associated antigens are secreted molecules or extracellular matrix related components which are not normally found in association with mature normal tissue.

Some tumor associated antigens are proteins expressed in earlier developmental stages of the tissue, and are not normally associated with the mature tissues (sometimes termed oncofetal proteins). Other tumor associated antigens are expressed by the normal mature cells, but are expressed in greater amounts by the cancer cells. Tumor associated antigens may be mutated forms of normally expressed cell markers or extracellular components. Still other tumor associated antigens are related to altered or unusual forms of glycosylation of proteins, lipids or extracellular components, or novel carbohydrate moieties.

Thus, tumor associated antigens can vary widely and define, at least in part, the type of tumor to be treated by the present invention. The variety of tumor types and tumor antigens which are expressed thereby is diverse and yet well studied in the cancer arts.

Many additional markers for tumors are under investigation, and once identified and characterized as being a tumor associated antigen, they are also a suitable target antigen for targeting immunotherapeutic to a desired tumor or metastases site.

Targeting of gene therapy vectors to cancer cells using anti-Lewis-Y antigen monoclonals has been reported. (Kurane S et al., *Jpn J. Cancer Res.* 89(11): 1212-9 (1998)). Similarly, targeting of liposomes using anti-ganglioside GM3 antibody or anti-Lewis-X antigen antibody has also been reported. (Nam, S. M, et al., *Oncol. Res.* 11(1):9-16 (1999).

As discussed below, methods in the art are known for taking an identified antigen to generate the appropriate antibodies which will bind specifically for that antigen. In this fashion, tumor antigens can be identified and monoclonal antibodies can be made which are useful in the present invention. For a review of the preparation of tumor antigens, see the teachings in *Human Cancer Markers*, The Humana Press Inc., eds. Sell and Wahren, 1982. Standard biochemical and molecular biological techniques applicable to preparing antigens and/or cytokines and the like can be found in, for example, Sambrook et al., (1989) *Molecular Cloning* $2^{nd}$ ed. (Cold Spring Harbor Press, CSH NY).

Tumor cell surface antigens may be specific for a class of tumors, or for an individual type of tumor. Many of the nucleic acid and/or amino acid sequences related to and encoding for tumor associated antigens are available from public computer databases which can be accessed via the Internet through various services, i.e. the NCBI (National Center for Biotechnology Information), and are generally identified by name and accession number (a few, non-limiting examples of the types of accessible sequence information are referred to by the comment "see Accession number").

Preferred tumor associated antigen targets include, and are not limited to, AFP (see Accession NP 001125), CA125 (see Accession NP 005890), CEA (see Accession AAA62835), CD19 (see Accession P15391), CD20 (see Accession P11836), CD44 (see Accession P16070), CD45 (see Accession P08575), EGF Receptor (see Accession P00533), $GD_2$, $GD_3$, GM1, GM2, Her-2/Neu (see Accession AAA58637), Ep-CAM (KSA) (see Accession P16422, AAA36151), IL-2 receptor (see Accession P14784, NP 000197, P01589), Lewis-Y, Lewis-X (CD 15), melanoma-associated proteoglycan MCSP (see Accession NP 001888), PSA (see Accession P07288), PMSA, Transferrin Receptor (see Accession NP 003218, NP 003225, AAF04564), Pancreatic Carcinoma Marker Protein GA733-1 (see Accession P09758), Folate receptor (see Accession NP 000793), L6 (see Accession P30408) and CO-029 (see Accession A36056, P19075).

Particularly preferred tumor associated antigen targets for targeting immunotherapeutics are $GD_2$, and KSA (Ep-CAM; KS1/4 antigen), as described herein.

Tumor associated antigen protein are commercially available, or can be generated using standard recombinant DNA and cell culture, protein expression techniques known in the art. For example, Sigma (St. Louis, Mo.) lists for sale Disialoganglioside GD2 (G 0776), Disialoganglioside GD3 (G 5904), monosialoganglioside GM1 (G 7641), monosialoganglioside GM2 (G 4651), Gastrointestinal Tumor Antigen Ca 19-9 (G 8660, G 8535), Carcinoembryonic antigen CEA (C4835), Lewis-X trisaccharide (L 5152), and Lewis-Y (L 7401).

Antibodies specific for many of these tumor associated antigens are available commercially. (Eg. USB, RDI, Accurate Chemical and Scientific Corp., Zymed Lab). For example, Sigma (St. Louis, Mo.) sells many monoclonal antibodies such as anti-AFP (A 8452), anti-CEA (C2331), anti-EGF receptor (E 3138), anti-IL-2 soluble receptor, (I 5652, I 5777, I 5902), anti-CD19 (F 3899), anti-CD20 (C8080), anti-CD44 (C7923), and anti-CD45 (C7556).

Even if not commercially available, using known methods of making monoclonal antibodies, antibodies specific for tumor associated antigens can be generated using the antigen as an immunogen. For example, anti-Lewis-Y antigen murine antibody heavy and light chain variable domains have been described (see Accession AAB25798 and AAB25799). Similarly, anti-asialo GM1 ganglioside murine antibody heavy and light chain variable domains (see Accession AAD09194 and AAD09195). A crystal structure has been solved for an anti-GD2 ganglioside monoclonal antibody heavy and light chain (see Accession 2554841, 2554842). Antibodies have been reported which bind the folate receptor (binding protein), identified as a marker for ovarian cancer (see Accession NP 000793). Anti-CA125 monoclonal variable region heavy and light chain nucleic acid sequence has also been reported, and used for insertion into a cassette vector (see Accession AAB33454, 33455).

Particularly preferred antibodies are the ch14.18 and KS1/4 antibodies described herein.

b) Monoclonal Antibody and Antigen Binding Portions thereof, and the Like

Since the advent of methods for generating monoclonal antibodies first published by Kohler and Milstein, improved methods have become well known in the art. (See for example, Dean, C. J. in *Methods in Molecular Biology* Vol. 80: *Immunochemical Protocols*, $2^{nd}$ ed. (Pound, J. D. editor, Humana Press, Inc., Totowa N.J., 1998) chapter 4; and Ausbel, F. M. et al., *Short Protocols in Molecular Biology*, $2^{nd}$ ed. (Current Protocols, John Wiley & Sons, NY N.Y., 1992) chapter 11). It is now routine practice to generate monoclonal antibody which binds to a particular antigen. Screening protocols have also improved for the selection of high-affinity binding antibodies, if desired.

Typically the host for production of hybridomas are mouse derived, or other rodents.

One barrier to repeated treatment with murine monoclonals to human patients is the HAMA (human anti-mouse antibodies) generated by the patient in response to the treatment. Methods to over come this barrier include humanization of murine antibody proteins by substituting antigenic amino acids of the mouse protein for human protein sequences, that are assumed to be less antigenic. Other methods involve the grafting of the binding specificity determining amino acid residues or regions into human protein frameworks.

The ability to express antibody protein in phage display systems allows for selection of antibodies which have been subjected to mutagenesis to either improve binding or to reduce immunogenicity (See for example *Antibody Engineering* (McCafferty, J. et al. editors, Oxford University Press, 1996). Recently, the substitution of human immunoglobulin genes into transgenic mice has allowed the use of murine hosts to generate antibodies, and thus monoclonal antibodies, that are of human nucleic acid sequence origin.

Antibodies can also be reduced in size by fragmentation to allow for reduced antigenicity, or to create smaller therapeutic molecules. For example, a whole antibody protein can be reduce, either by digestion with the appropriate enzymes or by producing the smaller protein by recombinant DNA methods. Suitable fragments will include at least an antigen binding portion of the whole molecule, and can comprise Fab, F(ab)2, F(ab)3, Fv or single chain Fv (single chain antibody; SCA) constructs.

It is envisioned that all monoclonal antibody based components of the therapeutic agents for use in the methods of the invention for treating humans, can benefit from modification to reduce immunogenicity and potential HAMA, as described above.

It is also possible to utilize specific receptor protein which may specifically bind to a particular tumor associated antigen, as the targeting component of the immunotherapeutic agents described above. Functionally, a specific receptor may be as useful as a specific antibody for targeting depending upon receptor specificity and affinity for the target tumor associated antigen. Care should be taken to minimize the impact of cross-reactive binding to similar proteins that are not necessarily tumor associated.

c) Cytokines

In one embodiment the anti-tumor immunotherapeutic constructs of the invention incorporate a cell effector portion which is preferably a cytokine.

The effector component of the anti-tumor therapeutics of the invention can comprise any of a variety of cytokines for inducing a cytokine-specific biological response by a cell bearing a receptor for the cytokine. Cytokines are well characterized, and therefore, the invention is not to be construed as so limited. Cytokines include as a subclass the molecules referred to as chemokines. In the context of the present invention, a chemokine is considered a member of the cytokine superfamily. Therefore the term cytokine as used herein refers generically to both cytokines and chemokines. For a description of the cytokine arts, see Callard and Gearing, *The Cytokine Facts Book*, Academic Press, Inc., 1994. For a description of the chemokine arts, see Vaddi et al, *The Chemokine Facts Book*, Academic Press, Inc., 1997. Many of the nucleic acid and/or amino acid sequences related to cytokines are available from public databases which can be accessed via the Internet through various service, i.e. the NCBI (National Center for Biotechnology Information), and generally identified by name and accession number (a few, non-limiting examples of access to sequence information cited herein refer to this by the comment "see Accession" with reference to the identifying number).

Cytokines from mammals may be species specific, and can also vary within a species due to mutation and/or allelic variation. Suitable cytokine can be selected for use according to the species of mammal to be treated. Where multiple alleles exist, selection can be made according to cytokine activity, or a mixture of allelic variants can be employed as the cytokine of choice. Thus veterinary use of the methods of the invention can be tailored to the species of animal to be treated, or a selection of a cytokine from a more closely related species selected if one from the target species is not available. For human treatment, it is preferred that the human homolog is used where known.

Cytokines suitable for use in the present invention include, and are not limited to, BDNF (see Accession 4502393), CNTF (see Accession 4758020), EGF (see Accession p01133), Epo (see Accession 4503589), FGF (see Accession CAB61690), Flt3L, G-CSF (see Accession CAA27290), GM-CSF (see Accession 4503077), I-309/TCA-3, gamma-IP-10 (see Accession P02778), IFN alpha (see Accession P01563), IFN beta (see Accession P01574), IFN gamma (see Accession P01579), IL-1 through IL-18 (see Accession P01583, P01584, P01585, P08700, P05112, P05113, P05231, P13232, P41324, P15248, P22301, P20809, P29459, P46658, P35225, P40222, P40933, Q14005, NP002181, Q14116), LIF (see Accession AAC05174), LT (see Accession 4504031), MCP-1 through MCP-3, M-CSF (see Accession 4503075), MIF (see Accession 4505185), MIP-1alpha, MIP-1beta, MIP-2, NGF (see Accession 4505391), NT-3 (see Accession P20783), NT-4 (see Accession P34130), OSM (see Accession P13725), PBP (see Accession 4505621), PBSF, PGFD, PF-4, RANTES, SCF (see Accession P21583), TGF alpha (see Accession P01135), TGF beta (see Accession P01137), TNF alpha (see Accession P01375), Tpo (see Accession P40225) or VEGF (see Accession AAD03710).

Chemokines suitable for use in the invention include, and are not limited to, C10 (see Accession P33861), EMF-1 (see Accession P08317), ENA-78 (see Accession A55010), Eotaxin (see Accession BAA84579), GCP-2 (see Accession P80162), HCC-1 g1004267), I-309 (see Accession g4506833), IL-8 (see Accession AAA59158), IP-9 (see Accession CAA75510), IP-10 (see Accession 4504701), Lymphotactin (see Accession 4506853), MCP-1 (see Accession 4506841), MCP-2 (see Accession P80075), MCP-3 (see Accession CAB59723.1), MCP-4 (see Accession Q99616), MGSA (see Accession P09341), MIG (see Accession P35625), MIP-1alpha (see Accession P10855), MIP-1beta (see Accession P13236), MIP-2, NAP-2 (see Accession P20775), PF4 (see Accession 4505733), RANTES (see Accession 4506847), SCM-1 (see Accession P47992) or SDF-1 (see Accession P48061). Preferred cytokines for use in the present invention include IL-2 and IL-12, or biologically active fragments thereof, which retain at least a portion of the effector activity of the whole intact molecule.

A preferred cytokine for use in the invention is IL-2.

Suitable cytokines, for use in the methods of the invention can be prepared from the appropriate nucleic acid sequence using standard molecular biology techniques. Methods for gene expression are known in the art (for example see Goeddel, D. V. editor, *Methods in Enzymology* Vol 185: *Gene Expression Technology* (Academic Press, Inc., NY N.Y., 1991). Cytokines are also available from commercial sources (i.e. Sigma, St. Louis Mo.).

d) Anti-Tumor/Cytokine Immunotherapeutic

These anti-tumor immunotherapeutic agents suitable for practicing the invention incorporate a cell-effector component which is preferably a cytokine, linked to a tumor targeting component. Linkage of a tumor binding component with the effector component can be accomplished by a variety of methods.

1) Antibody Fusion Proteins

Immunotherapeutic anti-cancer reagents have been described which target cytokine function to a cell or tissues which bear tumor antigens, and by using the cytokine thereby to recruit an immune response against cells bearing, or associated with the tumor antigen. These immunotherapeutic agents are referred to as anti-tumor antigen/cytokine fusion proteins because the fusion protein comprises a fusion of a cytokine with a recombinant immunoglobulin (Ig) polypeptide chain which immunoreacts with a preselected tumor associated antigen.

As used herein, the immunotherapeutic anti-tumor antigen/cytokine fusion protein agent encompasses fusion constructs between antibody protein fragments which comprise at least an antigen binding portion, and cytokines which comprise at least an effector portion of the cytokine sufficient to retain the cytokine biological signaling function. Fusion proteins of the invention may be direct or may be bridged by a linker peptide or peptides.

Anti-tumor antigen/cytokine fusion proteins are known in the art, and in particular are described, for example, in U.S. Pat. No. 5,650,150 (Gillies), the disclosures of which relating to the preparation and use of fusion proteins are expressly incorporated herein by reference.

The fusion protein can be directed to any of a variety of tumor antigens that are cell surface antigens, and so the invention is not to be construed as so limited. For example the preparation of a fusion protein using a cytokine and an Ig heavy chain is known, as is the preparation of a recombinant Ig heavy chain derived from a monoclonal antibody. Additionally, the preparation of monoclonal antibodies is an established art, and it is known how to prepare such antibodies against tumor antigens. Teachings regarding the preparation of monoclonal antibodies include "Monoclonal Antibodies and Cancer Therapy", Alan R. Liss, Inc., eds, Reisfeld and Sell, 1985.

Typically, the Ig polypeptide chain is an Ig heavy or light chain polypeptide that comprises an N-terminal variable region specific for a cell bearing a cell surface tumor antigen. The fusion protein typically has the Ig polypeptide joined at is carboxy-terminus by a peptide bond to the amino terminal amino acid of the cytokine. Where the Ig polypeptide is a heavy chain, the Ig heavy chain further typically comprises CH1 and CH2 domains, and may optionally further contain a CH3 domain. However, if desired, such constant region domains can be eliminated to reduce immunogenicity, size, or non-specific binding of the resultant fusion protein construct. In order to facilitate heavy and light chain domain association, it may be desired to construct a linked Fv molecule, wherein a heavy chain Fv is tethered to a light chain Fv. The tether is between the carboxy end of one chain to the amino terminal of the other, and is long enough so as not to drastically sterically alter the antigen binding pocket after refolding/domain association.

A preferred fusion protein comprises the cytokine IL-2 and an Ig heavy chain that immunoreacts with the tumor associated antigen $GD_2$. In another embodiment, a preferred fusion protein comprises the cytokine IL-2 and an Ig heavy chain that immunoreacts with the tumor associated antigen Ep-CAM (also known as KSA, KS1/4 antigen). Exemplary fusion proteins of these embodiments are described below as ch14.18-IL-2 and KS1/4-IL-2, respectively.

2) Antibody Conjugates

Alternative immunotherapeutic constructs can be used in the methods and compositions of the invention. For example, utilizing the high affinity Biotin-avidin system, independent biotinylated proteins comprising a tumor associated antigen specific antibody chain linked to biotin (or avidin), and a cytokine linked to the appropriate conjugate (avidin or biotin) can be constructed using the appropriate linkage. In use, a biotinylated antibody protein can be combined with the cytokine protein in vitro or in vivo, before or after administration to create bi-functional immunotherapeutic having a tumor antigen binding component and an effector cytokine component, linked by the biotin-avidin complex.

Biotinylated antibodies and proteins are known in the art, and can be prepared using commercially available reagents. One feature of utilizing a biotinylated tumor antigen targeting antibody is that the biotin molecule has multiple avidin binding sites, which will allow for greater potentiation of the effector component, such as an avidin linked cytokine, to each bound antibody or the combined use of more than one effector component. Other direct chemical conjugation methods and reagents are also known in the art, and have been applied to conjugating antibodies to effector molecules, either directly, or with an intervening linker. (See for example, Haugland and You, in *Methods in Molecular Biology* Vol. 80: *Immunochemical Protocols*, 2$^{nd}$ ed. (Pound, J. D. editor, Humana Press, Inc., Totowa N.J., 1998) chapter 17; and Hermanson, G. T. *Bioconjugate Techniques* (Academic Press, Ny N.Y., 1996). Thus the immunotherapeutic agents of the invention also encompass biotinylated constructs, as described above, between antibody protein fragments which comprise at least an antigen binding portion, and cytokines which comprise at least an effector portion of the cytokine sufficient to retain the cytokine biological signaling function.

e) Other Immunotherapeutics

The anti-tumor immunotherapeutic agents suitable for use in the methods, compositions, and kits embodying the invention can incorporate an effector portion which is not a cytokine. It is envisioned that the cell effector component can also be a toxin or otherwise tumor damaging cytotoxic agent. Other useful anti-tumor therapeutics can thus include constructs between antibody protein fragments which comprise at least an antigen binding portion, and radioisotopes, immunotoxin, cytotoxic peptide or cytotoxic drugs.

1) Radiolabel-Antibody

Radioimmunoconjugates comprising tumor targeting monoclonal antibody and radio-label isotope have been used as anti-cancer agents. The antigen binding specificity of the monoclonal antibody provides the targeting capability to localize to tumor sites, while the radio-label provides the cytotoxic properties. (See Hermanson, G. T. *Bioconjugate Techniques* (Academic Press, Ny N.Y., 1996) chapter 8). These radioimmunoconjugates may be suitable for use as an anti-tumor therapeutic in the methods of the invention.

2) Immunotoxin-Antibody

Conjugates of monoclonal antibodies and protein toxins derived from a variety of sources are also being tested for anti-tumor treatments. (See Hermanson, G. T. *Bioconjugate Techniques* (Academic Press, Ny N.Y., 1996) chapter 8). Such conjugates may be suitable for use in the methods of the invention.

3) Drug Cytotoxin-Antibody

Conjugates of monoclonal antibodies and drug toxins chemically synthesized and/or purified from a variety of sources may also be used for anti-tumor treatments. (See Hermanson, G. T. *Bioconjugate Techniques* (Academic Press, Ny N.Y., 1996). Such conjugates may be suitable for use in the methods of the invention.

4) Multi-Specific Antibody

Manipulation of antibody fragments generated by enzymatic digestion, or by manipulating encoding DNA sequences, allows for the creation of bi-specific antibodies (BsAbs) which are hybrid molecules that combine two antibodies with different binding specificities. In this way, specific binding to a target tumor can be combined with binding to a cellular effector pharmaceutical (i.e. cytokine, drug or toxin) to localize treatment of the tumor cells. (See for example, French, R. R., in *Methods in Molecular Biology* Vol. 80: *Immunochemical Protocols*, 2$^{nd}$ ed. (Pound, J. D. editor, Humana Press, Inc., Totowa N.J., 1998) chapter 12). Such bi- or otherwise multifunctional antibody may be suitable for use in the methods of the invention.

2. Therapeutic Methods

Therapeutic methods of the present invention for treating tumor cells in tumors and tumor metastases are based on the combined use of angiogenesis inhibiting (anti-angiogenesis) therapy and anti-tumor immunotherapy. More than one type of angiogenesis inhibiting agent can be used in combination with more than one type of anti-tumor immunotherapy agent. The combined use can occur simultaneously, sequentially, or with the intervention of a period of time between the treatments. Any of the specific therapeutics may be administered more than once during a course of treatment. The method of the invention provides for the combined use of angiogenesis inhibiting therapeutics and anti-tumor immunotherapeutics which can result in a synergistic potentiation of the tumor cell proliferation inhibition effect of each individual therapeutic, yielding more effective treatment than found by administering an individual component alone. Thus, in one aspect, the method of the invention encompasses administering to a patient, in combination, an amount of an angiogenesis inhibiting agent and an anti-tumor immunotherapeutic that may not result in effective angiogenesis inhibition, or anti-tumor cell activity if given in that amount alone.

The method of the invention comprises a variety of modalities for practicing the invention in terms of the steps. For example, the antagonist and anti-tumor immunotherapeutic agent (such as a tumor antigen/cytokine fusion protein in a preferred embodiment) can be administered following admixture, ie, simultaneously, or can be administered sequentially, ie, separately. Furthermore, the antagonist and the fusion protein can be separately administered within a time interval of about 3 weeks between administrations, i.e., from substantially immediately after the first active agent is administered to up to about 3 weeks after the first agent is administered. Additionally, it is contemplated that the order can be varied, ie, that the $\alpha_v\beta_3$ antagonist could be administered prior to administration of the fusion protein, or that administration can be conducted in the reverse order.

In one embodiment, the method of the invention also encompasses administering to a patient in need of treatment of tumors or metastases an angiogenesis inhibiting amount of an angiogenesis inhibiting agent, such as an $\alpha_v\beta_3$ antagonist, and an amount of anti-tumor immunotherapeutic agent sufficient to elicit a biological response. For example, sufficient to elicit a cytokine-specific biological response where such as a bifunctional fusion protein having a cytokine and a recombinant immunoglobulin (Ig) polypeptide chain, wherein the Ig chain comprises a variable region specific for a tumor cell bearing a tumor associated cell surface antigen, and wherein the Ig chain is joined by a peptide bond to the cytokine. And where an immunotherapeutic agent comprises a cytotoxic agent, the amount can be such to elicit a cytotoxic-biological response in target tumor cells.

In another embodiment, the invention can be practiced in conjunction with surgical procedures where portions or all of a tumor mass has been removed. In this regard, the method can be practiced following a surgical procedure. Alternatively, the surgical procedure can be practiced during the interval between administration of the first active agent and the second active agent. Exemplary of this method is the combination of the present method with surgical tumor removal described below.

Treatment according to the method will typically comprise administration of the therapeutic compositions in one or more cycles of administration. For example, where a simultaneous administration is practiced, a therapeutic composition comprising both an $\alpha_v\beta_3$ antagonist and an anti-tumor immunotherapeutic is administered over a time period of from about 2 days to about 3 weeks in a single cycle. Thereafter, the treatment cycle can be repeated as needed according to the judgment of the practicing physician. Similarly, where a sequential application is contemplated, the administration time for each individual therapeutic will be adjusted to typically cover the same time period. The interval between cycles can vary from about zero to 2 months.

Administration can be accomplished by periodic unit dosages, by continuous infusion, peristaltic delivery, by bolus injection, and the like. Routes can include intravenous, subcutaneous, intramuscular, orthotopic injection, orthotopic infusion, oral application, and the like.

A therapeutic composition used in a method of this invention comprises the active agent in a pharmaceutically acceptable carrier, as is well known, and therefore the invention is not to be construed as limited with regards to the composition so long as the concentration of the active agent(s) in the composition is sufficient for delivery (administration) of the recited active agent in the amounts described herein.

Typically, the dosage of anti-tumor immunotherapeutic agent, such as an antigen targeting/cytokine fusion protein is 0.01 mg to 10 mg, preferably about 0.1 to 1 mg, and more preferably about 0.6 mg per kilogram body weight per day.

The dosage of anti-tumor immunotherapeutic agent, such as an antigen targeted cytotoxic agent can be typically 0.01 mg to 10 mg, preferably about 0.1 to 1 mg, and more preferably about 0.6 mg per kilogram body weight per day, where the dosage of radiation can be appropriately adjusted depending upon the desired radiation dose. Isotopes that have been found suitable for radiation treatment include 57-Cobalt; 67-Copper; 99-Technetium; 123-Iodide; 131-Iodide; and 111-Indium and the like. Radiopharmaceuticals and dosages will vary depending upon the radioisotope and the target tissue. Immunoradiation therapy of malignant neoplasms can utilize higher doses than traditional radiation therapy, since the immunotherapeutic is targeted to the tumor site and/or cell. For example, treatment of B-cell non-Hodgkin's lymphoma with a radioimmunotherapeutic that targets B-cells was found to have a maximum tolerated dose of 0.4 mCui/kg body weight (1 mCui=37 Mbq). (Witzig, T E et al., (1999) "Phase I/II trial of IDEC-Y2B8 radioimmunotherapy for treatment of relapsed or refractory CD20(+) B-cell non-Hodgkin's lymphoma" *J. Clin. Oncol.* 17(12): 3793-803. However, targeted radioimmuontherapy to specific tumor or tumor metastases can allow for higher tolerated doses, than the treatment of lymphomas. In nude mice, administration of two doses of 18.5 Mbq of 111-Indium-labeled antibody, was tolerated. (Saga T, et al., (1999) "Radioimmunotherapy of human glioma xenografts in nude mice by indium-111 labelled internalising monoclonal antibody" *Eur. J. Cancer* 35(8): 1281-5).

The typical dosage of an $\alpha_v\beta_3$ antagonist is 10 mg to 1000 mg, preferably about 20 to 100 mg, and more preferably about 50 mg per kilogram body weight per day.

It is understood that cancer is found throughout the animal kingdom, and that the principles described herein apply to all animals where angiogenesis can be inhibit by an $\alpha_v\beta_3$ antagonist and that cytokines in the immune system. Thus it is considered that the invention can be practiced on all mammals, and particularly on humans.

Furthermore, it is known that there are a wide variety of tumors which require vascularization in order to grow, and therefore are candidates for the combined therapy modality of the present methods. Tumors which can result in growths that induce angiogenesis include tumors arising from neuroectodermal, epithelial and the like tissues. Exemplary tumors and tumor metastases include adenoma, angiosarcoma, astrocytoma, epithelial carcinoma, germinoma, glioblastoma, glioma, hamartoma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma, teratoma, and the like tumors.

3. Therapeutic Systems

In one embodiment, the invention contemplates systems comprising packaging and/or kit which provides the reagents necessary for practicing the methods of the present invention. A kit for treating tumor cells in tumor or tumor metastases comprises a package of:

a) an angiogenesis inhibiting agent such as an $\alpha_v\beta_3$ antagonist capable of inhibiting angiogenesis in the tumor or tumor metastases;

b) an anti-tumor immunotherapeutic agent, such as a bifunctional fusion protein reagent having a cytokine and a recombinant immunoglobulin (Ig) polypeptide chain, wherein the Ig chain comprises a variable region specific for a tumor cell bearing a tumor associated cell surface antigen, wherein the Ig chain is joined by a peptide bond to the cytokine; and c) instructions for using the reagents in methods to treat tumors and tumor metastases.

A reagent in a kit of this invention is typically formulated as a therapeutic composition as described herein, and therefore can be in any of a variety of forms suitable for distribution in a kit. Such forms can include a liquid, powder, tablet, suspension and the like formulation for providing the antagonist and/or the fusion protein of the present invention. The reagents may be provided in separate containers suitable for administration separately according to the present methods, or alternatively may be provided combined in a composition in a single container in the package.

Similarly, such a package may contain in place of, or in addition to the components described above, any other anti-tumor immunotherapeutic agents, such as described above.

The package may contain an amount sufficient for one or more dosages of reagents according to the treatment methods described herein. Typically, a package will contain an amount sufficient for one cycle of treatment as described herein. Package labeling may indicate the combined or sequential use of the enclosed reagents for therapeutic treatment of tumor and/or metastases, according to the methods of the invention. Such package labeling can be affixed to each reagent vial, and/or to the complete package of materials.

A kit of this invention also contains "instruction for use" of the materials contained in the package. The instructions relate to the method of the combined use of the antagonist and the fusion protein for treating a tumor or tumor metastases according to the methods of the invention. Insofar as the methods can vary widely depending upon the tumor, the patient and the condition of the disease, the instructions can vary to specify procedures for administration accordingly. The invention is not to be considered as limiting as to the nature of the instructions other than the particularity regarding the combined use of the antagonist and the fusion protein according to the methods of the present invention.

Similarly, the reagents may include anti-tumor immunotherapeutic cytotoxic agents, such as tumor antigen binding antibody joined to radio-label isotope, or a cytotoxic agent such as a cytotoxic peptide or cytotoxic drugs and the like.

4. Preparation of Synthetic Peptides a. Synthesis Procedure

The linear and cyclic polypeptides listed in Table 1 below, were synthesized using standard solid-phase synthesis techniques as, for example, described by Merrifield, R B, (1969) "Solid-Phase Peptide Synthesis", *Adv. Enzymol. Relat. Areas Mol. Biol.*, 32:221-96; Merrifield, R B, (1969) "The synthesis of biologically active peptides and proteins", *JAMA* 210(7): 1247-54; and Fields, G. B. and Noble, R. L., (1990) "Solid phase peptide synthesis utilizing 9-fluorenyl-methoxycarbonyl amino acids", *Int. J. Peptide Protein Res.*, 35(3):161-214.

Two grams (g) of BOC-Gly-DArg-Gly-Asp-Phe-Val-OMe (SEQ ID NO: 1) were first dissolved in 60 milliliters (ml) of methanol to which was added 1.5 ml of 2 N sodium hydroxide solution to form an admixture. The admixture was then stirred for 3 hours at 20 degrees C. (20° C.). After evaporation, the residue was taken up in water, acidified to pH 3 with diluted HCl and extracted with ethyl acetate. The extract was dried over $Na_2SO_4$, evaporated again and the resultant BOC-Gly-DArg-Gly-Asp-Phe-Val-OH (SEQ ID NO: 2) was stirred at 20° C. for 2 hours with 20 ml of 2 N HCl in dioxane. The resultant admixture was evaporated to obtain H-Gly-DArg-Gly-Asp-Phe-Val-OH (SEQ ID NO: 3) that was subsequently dissolved in a mixture of 1800 ml of dichloromethane and 200 ml of dimethylformamide (DMF) followed by cooling to 0° C. Thereafter, 0.5 g of dicyclo-hexylcarbodiimide (DCCI), 0.3 g of 1-hydroxybenzotriazole (HOBt) and 0.23 ml of N-methylmorpholine were added successively with stirring.

The resultant admixture was stirred for a further 24 hours at 0° C. and then at 20° C. for another 48 hours. The solution was concentrated and treated with a mixed bed ion exchanger to free it from salts. After the resulting resin was removed by filtration, the clarified solution was evaporated and the residue was purified by chromatography resulting in the recovery of cyclo(Gly-DArg-Gly-Asp-Phe-Val) (SEQ ID NO: 4).

The following peptides, listed in Table 1 using single letter code amino acid residue abbreviations and identified by a peptide number designation, were obtained analogously: cyclo(Arg-Gly-Asp-DPhe-Val) (SEQ ID NO: 5); cyclo(Arg-Ala-Asp-DPhe-Val) (SEQ ID NO: 6); cyclo(Arg-DAla-Asp-Phe-Val) (SEQ ID NO: 8); cyclo(Arg-Gly-Asp-Phe-DVal) (SEQ ID NO: 7); and cyclo(Arg-Gly-Asp-DPhe-NMeVal) (where methylation is at the alpha-amino nitrogen of the amide bond of the valine residue) (SEQ ID NO: 11).

A peptide designated as 66203, having an identical sequence to that of peptide 62184, only differed from the latter by containing the salt HCl rather than the TFA salt present in 62184 (SEQ ID NO: 5). The same is true for the peptides 69601 and 62185 (SEQ ID NO: 6) and for 85189 and 121974 (SEQ ID NO: 11).

b. Alternate Synthesis Procedure i. Synthesis of cyclo-(Arg-Gly-Asp-DPhe-NMeVal) (SEQ ID NO: 11), TFA Salt

Fmoc-Arg(Mtr)-Gly-Asp(OBut)-DPhe-NMeVal-ONa (SEQ ID NO: 14) is synthesized using solid-phase Merrifield-type procedures by sequentially adding NMeVal, DPhe, Asp(OBut), Gly and Fmoc-Arg(Mtr) in a step-wise manner to a 4-hydroxymethyl-phenoxymethyl-polystyrene resin (Wang type resin) (customary Merrifield-type methods of peptide synthesis are applied). The polystyrene resin and amino acid residues precursors are commercially available from Aldrich, Sigma or Fluka chemical companies). After completion of sequential addition of the amino acid residues, the resin is then eliminated from the peptide chain using a 1:1 mixture of TFA/dichloromethane which provides the Fmoc-Arg(Mtr)-Gly-Asp(OBut)-DPhe-NMeVal-OH product (SEQ ID NO: 15). The Fmoc group is then removed with a 1:1 mixture of piperidine/DMF which provides the crude Arg(Mtr)-Gly-Asp(OBut)-DPhe-NMeVal-OH precursor (SEQ ID NO: 16) which is then purified by HPLC in the customary manner.

For cyclization, a solution of 0.6 g of Arg(Mtr)-Gly-Asp(OBut)-DPhe-NMeVal-OH (synthesized above) (SEQ ID NO: 16) in 15 ml of DMF (dimethylformamide; Aldrich) is diluted with 85 ml of dichloromethane (Aldrich), and 50 mg of $NaHCO_3$ are added. After cooling in a dry ice/acetone mixture, 40 µl of diphenylphosphoryl azide (Aldrich) are added. After standing at room temperature for 16 hours, the solution is concentrated. The concentrate is gel-filtered (Sephadex G10 column in isopropanol/water 8:2) and then purified by HPLC in the customary manner. Treatment with TFA (trifluoroacetic acid)/$H_2O$ (98:2) gives cyclo-(Arg-Gly-Asp-DPhe-NMeVal) (also referred to as "cyclo(RGDfN-MeV)" herein; SEQ ID NO: 11)×TFA which is then purified by HPLC in the customary manner; RT=19.5; FAB-MS (M+H): 589.

ii. Synthesis of "Inner Salt"

TFA salt is removed from the above-produced cyclic peptide by suspending the cyclo-(Arg-Gly-Asp-DPhe-NMe-Val) (SEQ ID NO: 11)×TFA in water followed by evaporation under vacuum to remove the TFA. The cyclic peptide formed is referred to as an "inner salt" and is designated cyclo-(Arg-Gly-Asp-DPhe-NMeVal) (SEQ ID NO: 11). The term "inner salt" is used because the cyclic peptide contains two oppositely charged residues which intra-electronically counterbalance each other to form an overall noncharged molecule. One of the charged residues contains an acid moiety and the other charged residue contains an amino moiety. When the acid moiety and the amino moiety are in close proximity to one another, the acid moiety can be deprotonated by the amino moiety which forms a carboxylate/ammonium salt species with an overall neutral charge.

iii. HCl Treatment to Give cyclo-(Arg-Gly-Asp-DPhe-NMeVal) (SEQ ID NO: 11)×HCl 80 mg of cyclo-(Arg-Gly-Asp-DPhe-NMeVal) (SEQ ID NO: 11) are dissolved in 0.01 M HCl five to six times and freeze dried after each dissolving operation. Subsequent purification by HPLC give cyclo-(Arg-Gly-Asp-DPhe-NMeVal) (SEQ ID NO: 11)×HCl; FAB-MS (M+H): 589.

iv. Methane Sulfonic Acid Treatment to Give cyclo-(Arg-Gly-Asp-DPhe-NMeVal) (SEQ ID NO: 11)×$MeSO_3H$ 80 mg of cyclo-(Arg-Gly-Asp-DPhe-NMeVal) (SEQ ID NO: 11) are dissolved in 0.01 M $MeSO_3H$ (methane sulfonic acid) five to six times and freeze dried after each dissolving operation. Subsequent purification by HPLC give cyclo-(Arg-Gly-Asp-DPhe-NMeVal) (SEQ ID NO: 11)×$MeSO_3H$; RT=17.8; FAB-MS (M+H): 589.

Alternative methods of cyclization include derivatizing the side group chains of an acyclic peptide precursor with sulfhydryl moieties, and when exposed to slightly higher than normal physiological pH conditions (pH 7.5), intramolecularly forms disulfide bonds with other sulfhydryl groups present in the molecule to form a cyclic peptide. Additionally, the C-terminus carboxylate moiety of an acyclic peptide precursor can be reacted with a free sulfhydryl moiety present within the molecule for producing thioester cyclized peptides.

TABLE 1

| Peptide Designation | Amino Acid Sequence | SEQ ID NO |
|---|---|---|
| 62181 | cyclo(GrGDFV) | 4 |
| 62184 (66203*) | cyclo(RGDfV) | 5 |
| 62185 (69601*) | cyclo(RADfV) | 6 |
| 62187 | cyclo(RGDFv) | 7 |
| 62186 | cyclo(RaDFV) | 8 |
| 62175 | cyclo(ARGDfL) | 9 |
| 62179 | cyclo(GRGDfL) | 10 |
| 121974 (85189*) | cyclo(RGDfN-MeV) | 11 |
| 112784 | cyclo(RGEfN-MeV) | 12 |
| 135981 | cyclo(RADfN-MeV) | 13 |

*The peptides designated with an asterisk are prepared in HCl and are identical in sequence to the peptide designated on the same line; the peptides without an asterisk are prepared in TFA. Lower case letters indicate a D-amino acid; capital letters indicate a L-amino acid.

5. Generation and Characterization of Tumor-Specific Antibody-Cytokine Fusion a. Proteins and Vasculature-Specific Integrin $\alpha_v$ Antagonist:

Construction and characterization of ch14.18-IL-2 and huKS1/4-IL-2 antibody-cytokine fusion proteins were described previously (Xiang, R., et al., (1997); Gillies, S., et al., (1992) supra). Antigen binding characteristics of both constructs were identical to those of their respective antibodies and the specific EL-2 activity was equivalent to commercially available rhIL-2. The integrin $\alpha_v\beta_3$ antagonistic cyclic peptide 121974 (cyclo(RGDfN-MeV)) (SEQ ID NO: 11) and the control peptide 135981 (cyclo(RADfN-MeV) (SEQ ID NO: 13) were synthesized and characterized.

6. Cell Lines and Animal Models

All cell lines and respective animal models were established substantially as previously described (Becker, J. C., et al., (1996); Xiang, R., et al., (1996); Lode, H. N., et al., (1998) supra). The absence of integrin $\alpha_v\beta_3$ on NXS2 and CT26-KSA cells was demonstrated using anti-mouse CD61 (integrin $\beta_3$ chain) antibody (Pharmingen, La Jolla, Calif.). Both cell lines revealed no signal (1 µg anti-mouse CD61 mAb/$10^6$ cells) in FACS analysis in contrast to integrin $\alpha_v\beta_3$-positive B16FG3 and B78-D14 murine melanoma cells used as positive controls. Furthermore, NXS2 cells were unable to adhere to plastic coated with anti-mouse CD61 mAb (10 µg/ml 4° C., 24 h) in contrast to anti-$GD_2$ antibody ch14.18 (10 µg/ml, 4° C., 24 h) used as positive control. However, all tumor cells express $\alpha_v$ integrin by FACS and adhere on vitronectin, indicating the presence of integrin $\alpha_v\beta_5$.

For all surgical procedures, mice were anesthetized by ketamine injection (100 mg/kg i.p.) and simultaneous Metofane inhalation (Pitman-Moore, Mundelein, Ill.). Osmotic pumps (ALZET®, model 2001, Palo Alto, Calif.) for the administration of the integrin $\alpha_v$ antagonist and the control peptide were used at a delivery rate of 17.5 µg/h. These pumps were handled according to the manufacturer's guidelines and implanted in the dorsal subcutaneous tissue under sterile conditions. All pumps were replaced on day 7 after implantation and removed at day 10 of the anti-vascular treatment. All animal experiments were performed according to the NIH *Guide for the Care and Use of Laboratory Animals*.

7. Histology and Immunohistochemistry

Acetone-fixed, frozen sections of primary tumors were incubated with 4% goat serum to block non-specific binding. Incubations with anti-mouse CD31 and anti-mouse CD45 mAbs (Pharmingen, La Jolla, Calif.) (1:100) and subsequent staining with rhodamine-labeled goat anti-rat antibody (1:300) were performed in a humidified chamber at room temperature. Each incubation was followed by washes with PBS (×3). Vessel and white blood cell counts per high power field (HPF) were determined microscopically at 200× magnification (Brooks, P. C., et al., (1995) "Anti-integrin alpha v beta 3 blocks human breast cancer growth and angiogenesis in human skin", *J. Clin. Inves.* 96, 1815-1822). Representative areas were photographed at 200× (vessels) and 800× (white blood cells), respectively.

8. Primary Tumors Regress only in Mice Treated with Integrin $\alpha_v$ Antagonist Combined with Antibody IL-2 Fusion Proteins The synergistic effect of angiogenesis inhibiting therapy (integrin $\alpha_v$ antagonist) and immunotherapy (antibody IL-2 fusion proteins) was determined in mice with established subcutaneous tumors (110-130 µl) in all three syngeneic models, respectively.

FIG. 1, graphically depicts the effect of a combined therapy with anti-angiogenic $\alpha_v$ integrin antagonist and anti-tumor immunotherapeutic compartment-specific immunotherapy with antibody-IL-2 fusion proteins on primary tumors. FIG. 1A depicts results from primary tumors induced by subcutaneous injection ($2\times10^6$) of NXS2 neuroblastoma. FIG. 1B depicts results from primary tumors induced by subcutaneous injection ($2\times10^6$) of CT26-KSA colon carcinoma. FIG. 1C depicts results from primary tumors induced by subcutaneous injection ($2\times10^6$) of B78-D 14 melanoma cells. The treatment of established tumors (110-130 mm³) was initiated by daily intravenous injections of the tumor-specific antibody-IL-2 fusion proteins huKS1/4-IL-2 (10 µg, colon carcinoma) and ch14.18-IL-2 (5 µg, neuroblastoma, 10 µg, melanoma) (×5) and continuous subcutaneous infusion of the vasculature-specific integrin $\alpha_v$ antagonist or the control peptide with an osmotic pump for 7 days at 17.5 µg/h (top). The time of treatment initiation is indicated by a black arrow. The size of the primary tumors of mice in each experimental group (n=6) was determined by microcaliper measurements (width×length×width/2) (Mean±Standard Error). The regression in primary tumor size of mice receiving the combination treatment compared to the size of established tumors at the time of treatment initiation was statistically significant in the three different syngeneic tumor models (P<0.001, Wilcoxon Rank-Sum Test) in contrast to all controls (P>0.05).

First, suboptimal amounts for each therapeutic modality were established and their subsequent use in combination initiated. Only mice treated with the integrin $\alpha_v$ antagonist and the IL-2 fusion proteins presented with a tumor regression in all three models ranging from 50 to 90% (P<0.001). In fact, half the animals inoculated with neuroblastoma and colon carcinoma cells entirely rejected their primary tumors data not shown. This was in contrast to each strategy being used as monotherapy that, at best, delayed growth compared to the control group, respectively. The effect of each treatment modality and their combination on vascular and tumor compartments was subsequently analyzed.

Histology following combined anti-angiogenic and tumor-specific immunotherapy of established primary neuroblastoma tumors, surgically removed 20 days after tumor cell inoculation was performed. Briefly, formalin-fixed primary tumors were subjected to paraffin embedding and subsequent hematoxylin/eosin staining. Necrotic areas and leukocyte infiltrates were identified.

FIG. 2 graphically depicts the effect of combined anti-vascular and anti-tumor immunotherapeutic therapies on vascularization and anti-tumor immune response. Mice (n=6) with established primary neuroblastoma tumors received the combined treatment with vasculature-specific integrin cc, antagonist, a non-specific peptide control and tumor-specific ch14.18-IL-2 fusion protein, as described for FIG. 1, including controls that received each therapy alone. At the end of the treatment, s.c. tumors were removed surgically. Frozen sections of each tumor were analyzed by immunohistochemistry using antibodies specific for blood vessel endothelial cells (CD-31) and for leukocyte infiltration (CD45), respectively. The latter is a well-established marker for the tumor compartment-specific immune response induced by the ch14.18-IL-2 fusion protein (Becker, J. C., et al., (1996) supra; Xiang, R., et al., (1996) supra; Lode, H. N., et al., (1998) supra).

Figure 2A:
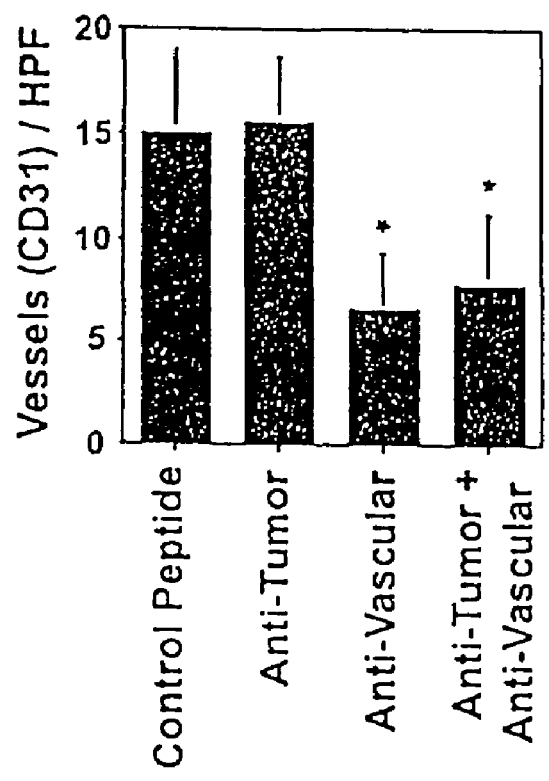
FIG. 2A depicts results for blood vessel density of primary tumors following vascular and tumor compartment treatment with either the integrin $\alpha_v$ antagonist, ch14.18-IL-2 fusion protein and a combination thereof (*P<0.001, Student's T-test).
Figure 2B:
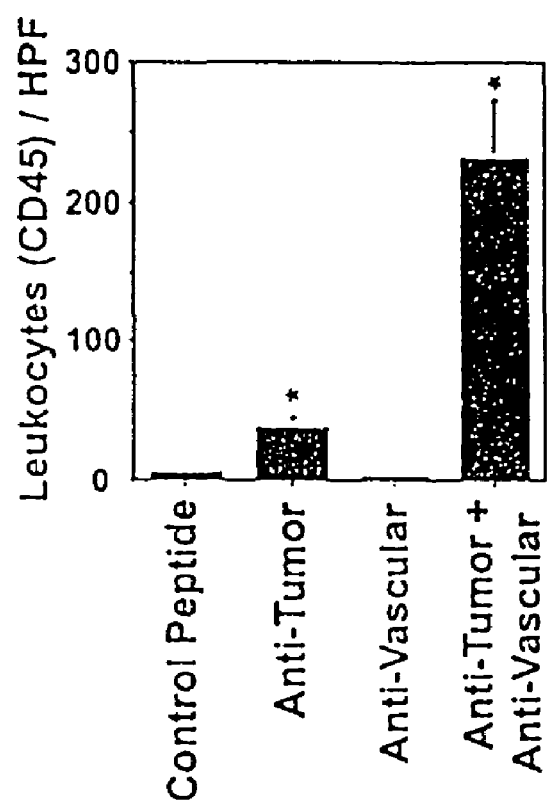
FIG. 2B depicts results for leukocyte infiltration of primary-tumors after vascular and tumor compartment treatments, respectively (*P<0.001, Student's T-test).

FIG. 2A depicts results for blood vessel density of primary tumors following vascular and tumor compartment treatment with either the integrin a, antagonist, ch14.18-IL-2 fusion protein and a combination thereof (*P<0.001, Student's T-test). FIG. 2B depicts results for leukocyte infiltration of primary-tumors after vascular and tumor compartment treatments, respectively (*P<0.001, Student's T-test).

Mice receiving the integrin $\alpha_v$, antagonist showed a 50% decrease in vascularization (FIG. 2) coincident with a growth delay of primary tumors, demonstrating effective targeting of the vascular compartment. In this case, the tumor compartment was not affected directly (FIG. 1). In contrast, mice treated only with the anti-GD2-IL-2 fusion protein, revealed a distinct leukocytic infiltrate, a well-established characteristic of this anti-tumor compartment-directed therapy (Becker, J. C., et al., (1996) supra; Xiang, R., et al., (1996) supra; Lode, H. N., et al., (1998) supra), leading to a substantial reduction in s.c. tumor growth (FIG. 1).

However, only mice treated with the combination of integrin $\alpha_v$ antagonist and anti-GD2-IL-2 fusion protein revealed a five-fold increase in white blood cell infiltration into the tumor compared to mice treated with anti-GD2-IL-2 fusion protein alone and showed a similar decrease in vascularization. The increase in inflammatory cells was demonstrated by histology and immunohistochemistry, and was attributed to an influx of macrophages, a pattern frequently seen in necrotic tissues during removal of cellular debris. In fact, such necrotic areas were only present in tumors following the combination treatment in contrast to controls treated with each component separately.

9. Sequential and Simultaneous Vascular and Tumor Targeting Induces Eradication of Spontaneous Hepatic Metastases In addition to a successful treatment of primary tumors, the more relevant question is whether distant metastases are affected by such a combined anti-vascular and anti-tumor-specific treatment strategy. This was addressed in the neuroblastoma model, characterized by spontaneous hepatic metastases. For this purpose, treatment of the primary tumor with the anti-angiogenic integrin $\alpha_v$, antagonist was sequentially combined with anti-tumor immunotherapy by the antibody IL-2 fusion protein.

Figure 3:
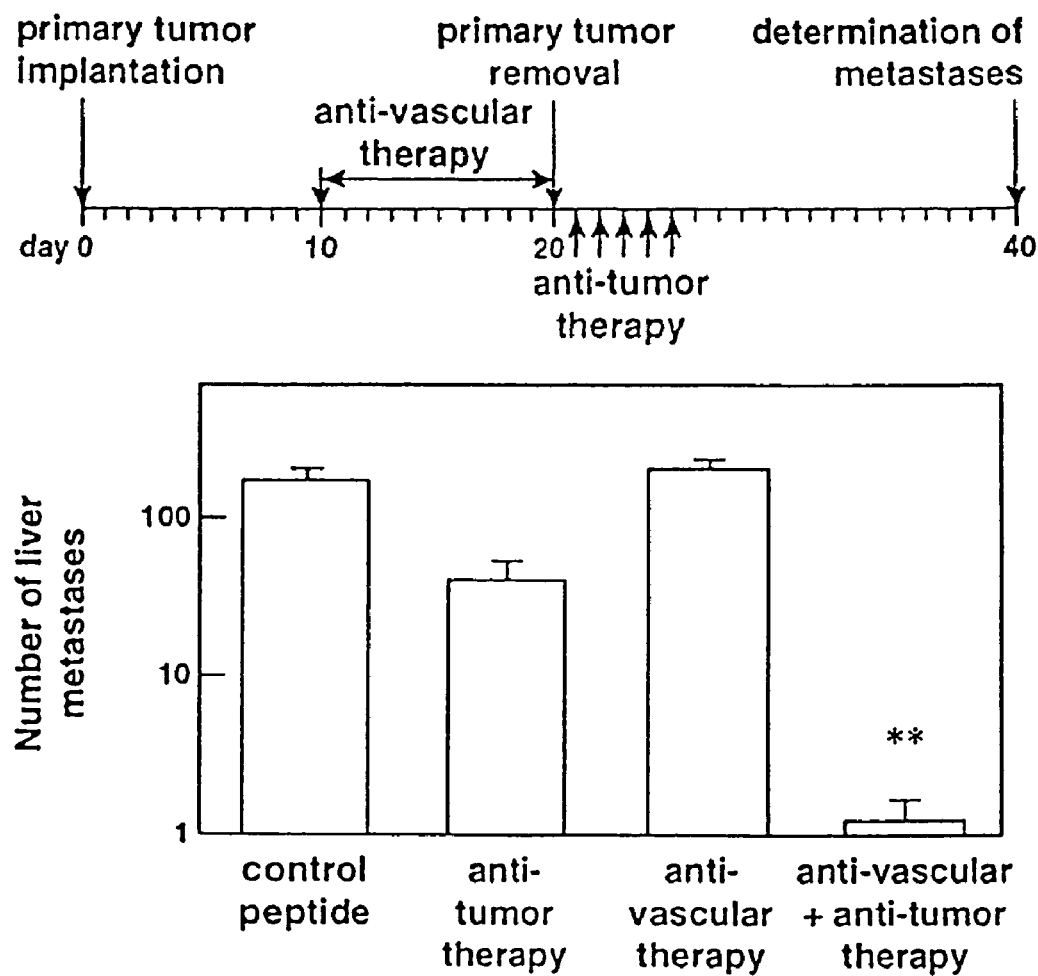
FIG. 3 graphically depicts the effect of a sequential combination of anti-angiogenic $\alpha_v$ integrin antagonist and anti-tumor compartment-specific immunotherapy with antibody-IL-2 fusion protein on spontaneous hepatic neuroblastoma metastases. The number of spontaneous liver metastases was determined by macroscopic counts of liver foci (n=8) (**P<0.01, Wilcoxon Rank-Sum Test).

FIG. 3 graphically depicts the effect of a sequential combination of anti-angiogenic $\alpha_v$ integrin antagonist and anti-tumor compartment-specific immunotherapy with antibody-IL-2 fusion protein on spontaneous hepatic neuroblastoma metastases. The anti-vascular treatment was initiated in mice with established primary tumors, as described for FIG. 1 for a total of 10 days. After surgical removal of the primary tumors, mice received the tumor compartment-specific immunotherapy by daily i.v. injections of 5 µg ch14.18-IL-2 fusion protein (×5). The number of spontaneous liver metastases was determined by macroscopic counts of liver foci (n=8) (**P<0.01, Wilcoxon Rank-Sum Test).

Only mice treated sequentially with both agents presented with a 1.5-2 log decrease in hepatic metastases in contrast to all controls, where treatment with each agent used as monotherapy was ineffective (P<0.01) (FIG. 3). In fact, 4/8 mice subjected to the combined therapy revealed a complete absence of hepatic metastases, while the remaining animals showed only 1-5 small metastatic lesions. In essence, similar results were obtained by simultaneous combinations of the integrin $\alpha_v$, antagonist with the ch14.18-IL-2 fusion protein (FIG. 4 top).

Figures 4A, 4B:
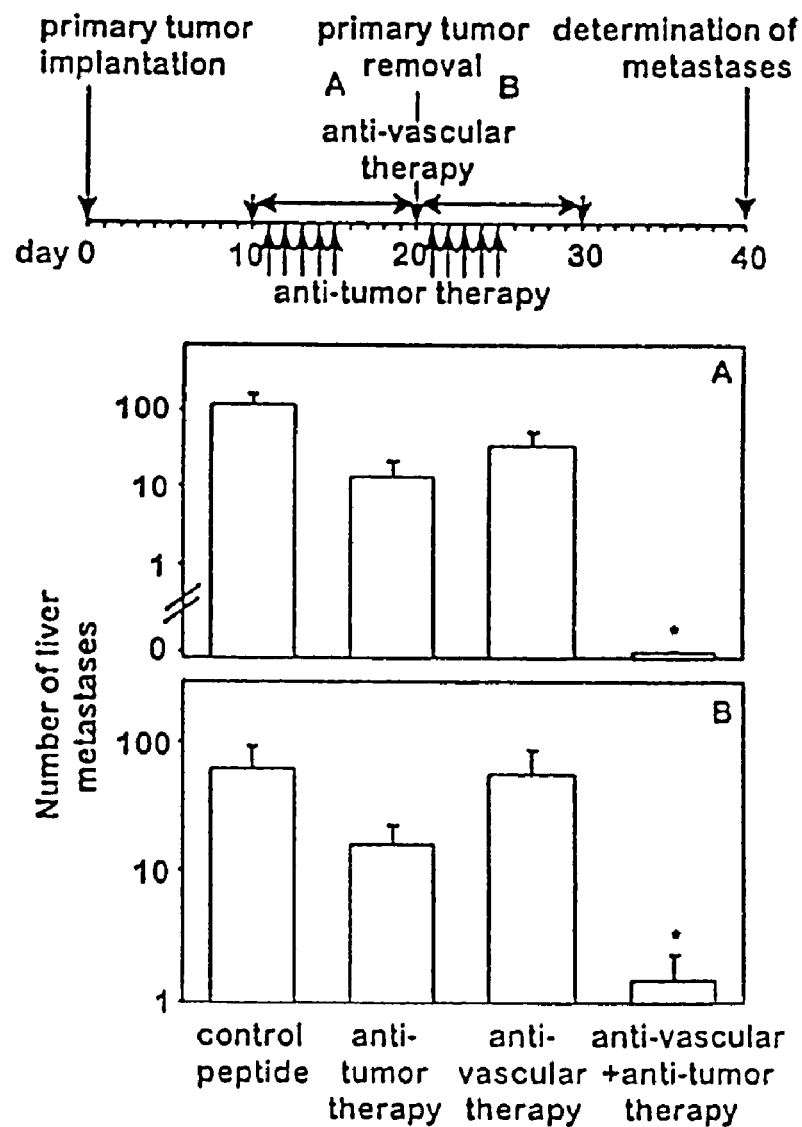
FIG. 4 graphically depicts the effect of the substantially simultaneous combination of anti-angiogenic integrin $\alpha_v$ antagonist and anti-tumor compartment-specific immunotherapy with antibody-IL-2 fusion protein on spontaneous hepatic neuroblastoma metastases. Results from treatment with integrin or, antagonist (17.5 μg/h) and tumor-specific ch14.18-IL-2 fusion protein (5 μg×5) initiated before (FIG. 4A) or after (FIG. 4B) removal of the primary tumor is shown. Spontaneous liver metastases were determined by macroscopic counts of liver foci (n=8)(*P<0.01, Wilcoxon Rank-Sum Test).

FIG. 4 graphically depicts the effect of the simultaneous combination of anti-angiogenic integrin $\alpha_v$ antagonist and anti-tumor compartment-specific immunotherapy with antibody-IL-2 fusion protein on spontaneous hepatic neuroblastoma metastases. Spontaneous metastases were induced following induction of primary tumors with $2 \times 10^6$ NXS2 neuroblastoma cells s.c. Treatment with integrin or, antagonist (17.5 µg/h) and tumor-specific ch14.18-IL-2 fusion protein (5 µg×5) initiated before (FIG. 4A) or after (FIG. 4B) removal of the primary tumor. Spontaneous liver metastases were determined by macroscopic counts of liver foci (n=8) (*P<0.01, Wilcoxon Rank-Sum Test).

Only mice treated with both agents revealed either a complete absence (FIG. 4A) or a >1.5 log decrease (FIG. 5B) in hepatic metastases (P<0.01), depending on their administration prior or post primary tumor removal. This is in contrast to all controls where treatment was ineffective when each agent was used as monotherapy.

10. Synergistic Combination and Effective Therapy

Disruption of blood vessels in the vascular compartment of malignant tumors is a powerful strategy to combat cancer. By targeting the endothelial cells of the tumor vasculature, the tumor can be successfully treated. A peptide antagonist, targeting the vasculature through interaction with $\alpha_v$ integrins expressed on angiogenic blood vessels (Brooks, P. C. et al., (1994) *Science* supra; Friedlander, M., et al., (1995) supra) suppressed blood vessel formation and dramatically regressed subsequent tumor growth. This was demonstrated by treating three aggressively growing primary tumors and one spontaneously metastasizing tumor. While the integrin $\alpha$ antagonist used was primarily directed to $\alpha_v\beta_3$, it also binds the closely related integrin $\alpha_v\beta_5$. The colon carcinoma and neuroblastoma tumors examined are clearly lacking $\alpha_v\beta_3$, but likely expresses some $\alpha_v\beta_5$. The melanoma model also expresses $\alpha_v\beta_3$. However, the effect of this integrin antagonist was clearly restricted to the tumor vasculature in all three animal models as demonstrated for the neuroblastoma model (FIG. 2). Importantly, the anti-tumor effect of targeting the tumor vasculature is amplified by a simultaneous attack on the tumor compartment, which is effective against both primary tumors and spontaneous metastases. This is particularly relevant, since removal of the primary tumor prior to treatment increased growth and dissemination of neuroblastoma metastases, a finding well documented in other tumor models due to a decrease in circulating levels of angiogenesis inhibitors following excision of the primary tumor (Holmgren, L., et al., (1995) supra; Folkman, J., (1995) supra). The simultaneous targeting of the vascular and tumor compartments proved very effective, since it combines a decrease in tumor cell nourishment with the active destruction of tumor cells, leading to a regression of primary tumors and the eradication of distant metastases. This is in contrast to a single vascular compartment-directed approach using two different anti-angiogenic treatment strategies that resulted only in suppression of s.c. tumor growth in a syngeneic model (Mauceri, H. J., et al., (1998) "Combined effects of angiostatin and ionizing radiation in antitumor therapy", *Nature* 394, 287-291).

In the present strategy, the tumor compartment-specific response is mediated by inflammatory cells that are activated and directed to the tumor microenvironment by the tumor-specific antibody-IL-2 fusion proteins. Importantly, the anti-angiogenic strategy, although quite effective in growth suppression of primary tumors with a well-established vascular supply, lacks a similar efficacy against distant micrometastases when used as monotherapy (FIGS. 3, 4). However, in such a minimal residual disease setting with small tumor loads characterized by poor vascularization, the anti-tumor compartment treatment arm used in the combination therapy is quite effective when used as monotherapy (Xiang, R., et al., (1997) supra; Lode, H. N., et al., (1998) supra). In this situation, one role of anti-angiogenic treatment is to suppress micrometastasis-induced neovascularization and subsequent enlargement of metastatic foci (Volpert, O. V., et al., (1998) supra). This, in turn, facilitates the eradication of such micrometastases by tumor compartment-directed therapies, which are optimally effective in the minimal residual disease setting (Becker, J. C., et al., (1996) supra).

Effective treatments of primary tumors and disseminated metastases remain a major challenge in clinical oncology. The results in this report show that combinations of specific anti-angiogenic and immunotherapies synergize in regression of primary tumors and eradication of micrometastases. Since both treatment modalities, i.e. $\alpha_v$ integrin antagonists and antibody-interleukin-2 fusion proteins, are currently under clinical evaluation as monotherapies, the synergy of their combination provides a novel and effective tool for cancer therapy.

The forgoing examples describing certain embodiments of the invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

What is claimed is:

1. A method for treating a tumor cell in a patient comprising administering to said patient a tumor cell proliferation inhibiting amount of:
   a) an angiogenesis inhibiting agent, which is an $\alpha_v\beta_3$ antagonist; and
   b) an anti-tumor immunotherapeutic agent which is a fusion protein comprising cytokine IL-2 and an Ig heavy chain that immunoreacts with a tumor associated antigen target, wherein said angiogenesis inhibiting agent and said anti-tumor immunotherapeutic agent are administered concurrently.

2. The method of claim 1 wherein said administration is effected after a tumor or tumor metastases has been surgically removed from said patient.

3. The method of claim 1 wherein said angiogenesis inhibiting agent is administered at a dosage of 10 mg to 1000 mg per kilogram body weight per day.

4. The method of claim 1 wherein said anti-tumor immunotherapeutic agent is administered at a dosage of 0.01 mg to 10 mg per kilogram body weight per day.

5. The method of claim 1 wherein said angiogenesis inhibiting agent has the amino acid residue sequence cyclo Arg-Gly-Asp-DPhe-NMeVal.

* * * * *